United States Patent [19]

Melillo

[11] Patent Number: 4,681,752

[45] Date of Patent: Jul. 21, 1987

[54] CAPSULES CONTAINING THE ACTIVE PRINCIPLE OF AN ALLERGEN, AND PROCESS FOR THEIR PREPARATION

[75] Inventor: Gaetano Melillo, Naples, Italy

[73] Assignee: Laboratorio Farmaceutico Lafarma S.a.S., Milan, Italy; a part interest

[21] Appl. No.: 597,241

[22] Filed: Apr. 4, 1984

Related U.S. Application Data

[63] Continuation-in-part of Ser. No. 379,269, May 17, 1982, abandoned.

[30] Foreign Application Priority Data

Jun. 4, 1981 [IT] Italy ............................... 22136 A/81

[51] Int. Cl.$^4$ .................... A61K 9/48; A61K 9/72; A61K 9/44; A61K 39/36
[52] U.S. Cl. ...................................... 424/453; 424/91
[58] Field of Search ...................... 424/37, 91, 93, 88, 424/92, 15; 604/58; 514/826, 962

[56] References Cited

U.S. PATENT DOCUMENTS

| | | | |
|---|---|---|---|
| 3,148,121 | 8/1964 | Strauss | 424/91 |
| 3,953,588 | 4/1976 | Nieschulz et al. | 424/91 |
| 3,995,023 | 10/1976 | Nieschulz et al. | 424/91 |
| 4,350,686 | 9/1982 | Relyveld | 424/88 |

FOREIGN PATENT DOCUMENTS 1182779  9/1966  United Kingdom ................ 604/58

OTHER PUBLICATIONS

Physicians Desk Reference, 34th edition, pp. 881–882, 1980.

*Primary Examiner*—Shep K. Rose
*Attorney, Agent, or Firm*—Bucknam and Archer

[57] ABSTRACT

Capsules to be administered through an inhaler, or inhaler tube or nasal spray, containing a finely subdivided powder mixture of the active principle of one or more allergens, uniformly dispersed and incorporated into at least an excipient are described. The capsules have no bronchoconstrictive or irritating action on the nasal mucous membrane and are more effective than allergens administered in solution. The method of preparation is also described.

7 Claims, No Drawings

CAPSULES CONTAINING THE ACTIVE PRINCIPLE OF AN ALLERGEN, AND PROCESS FOR THEIR PREPARATION

This application is a continuation-in-part of U.S. Ser. No. 379,269, filed May 17, 1982, now abandoned.

This invention concern capsules containing the active principle of an allergen, and the process for their preparation.

In particular, this invention concerns capsules, which contain the active principle of an allergen, and which are particularly suitable to be administrated by inhalation.

As everybody knows, when a patient, who suffers from asthma or allergic rhinitis, inhales through his respiratory system the substance to which he is sensitive, a cell reaction takes place. This reaction leads to the degranulation of the mast cells and to the release in the tissues of substance, which trigger off the obstruction of the respiratory system, bronchial spasm and/or rhinitis. In order to avoid or limit this cell reaction, a therapy has been carried on, in these last few years, with great success. It is the specific hyposensitization, which consists, as everybody knows, in administering to the patient increasing doses of the allergen to which he is sensitive.

The administration of the allergen is generally carried our either parenterally or by atomization and inhalation of an aqueous solution of the allergen. Unfortunately, there are serious drawbacks to both types of administration.

As far as hyposensitization therapy by parental administration is concerned, here are the main drawbacks:

(a) systemic reactions, which could even lead to an anaphylactic shock, might occur, owing to an error in the dosage, or to an imperfect execution, or to an abnormal biological reactivity of the patient;

(b) the administration must be absolutely made under medical control, or better under the control of the specialist in allergology because of its well known potentially dangerous reaction;

(c) the parenterally administered allergen does not get directly to the target organ where the pathological process takes place.

As far as the administration of the allergen by inhalation is concerned, even if we cannot deny its satisfactory results in the reduction of bronchial reactivity in some asthmatic patients, we must point out the following drawbacks: first of all, it implies the use of bulky and specialized equipment (atomizer) and, moreover, it causes a reduction in the activity of the allergen due to its frequent instability in aqueous solution. Moreover, the administration of raw material, e.g. culture in the case of mites, presents disadvantages as well: the administration of raw material is difficult in itself; the quantity of the active principle is variable; the presence of extraneous material, for example culture medium, can involve undesirable and uncontrollable phenomena, such as non specific irritation.

The object of the present invention is to provide a system of administration which allows the active principle of the allergen in the anhydrous state to come directly in contact with the target organ, where the pathological process is taking place.

In particular, the object of the present invention is to provide a form of the allergen which, without modifying its biological activity, allows to put its active principle, in the anhydrous state, directly in contact with tha place of the pathological process, that is to say with the upper and lower respiratory system.

It has now been found, and this is the subject of this invention, that it is possible to obtain this and other objects by using capsules, containing the active principle of one or more allergens, diluted in one or more excipients, free from any bronchoconstrictive action and non-irritant of the nasal mucous membrane.

Capsules thus obtained are administered by a normal inhaler or turbo inhaler, many types of which are aommonly available on the market. The capsules can be used both for therapeutic and diagnostic purposes, that is provocation tests.

The term allergen as used in the present specification and in the claims, means an antigen, a natural or synthetic substance or the active principle therein or derived therefrom which is antigenic (i.e. gives rise to an immunological reaction) and which has the capacity to produce a hypersensitivity reaction.

The allergens are supplied by several manufactures such as Diephuis Laboratorium, Allergon AB etc.

They are generally extracted from the culture or from the dust collected in individual patients' houses.

The active principle of an allergen can be prepared by extraction of the active constituents from animal or vegetable substance with a suitable menstruum. Temperature, pH value, extracting time, saline concentration of the menstruum during the extraction process change from allergen to allergen. For example, as far as mites are concerned, it can be far more advantageous to carry out the extraction with an aqueous solution at pH 7.2, at a temperature of +4° C., at a concentration of the solution, containing monobasic and dibasic sodium phosphate, equivalent to 0.15M, and to stir it for 24 hours.

The active principle of the allergen dissolves in aqueous solution and, after subsequent centrifugations and filtrations, it looks like a clear and homogeneous extract, which can be dehydrated, for example by freeze-drying.

The active principle of any allergen can be used to prepare the capsules, subject of this invention.

Just to give some examples, we mention mite allergens, such as *Dermatophagoides pteronyssinus* and *Dermatophagoides farinae,* which are the principal allergenic components of the house dust; pollen allergens, such as Short Ragweed (*Ambrosia elatior*), Bent grass (*Agrostis maritima*), Carpet bent (*Agrostis stolonifera*), Blue grass Kentucky (*Poa pratensis*), Orchard grass (*Dactylis glomerata*), Velvet grass (*Holcus lanatus*), Timothy grass (*Phleum pratense*), Canary grass (*Phalaris Canariensis*), Perennial Rye grass (*Lolium perenne*), Rye grass Italian (*Lolium multiflorum*), meadow Fescue grass (*Festuca pratensis*), Fescue sheep (*Festuca ovina*), Bermuda grass (*Cynodon dactylon*), Red Top grass (*Agrostis Alba*), etc; animal danders, moulds and others.

The allergens are commercially available as a product freeze-dried to a water content of 3–10% and of 85–98% purity, the remainder consists of coltivation media or plant parts.

The excipients can be selected within a wide range of known compounds, provided that they do not cause, as far as they are concerned, bronchoconstriction, irritating actions on the nasal mocous membrane, and other side-effects.

Excipients, which can be advantageously used in the preparation of the capsules, are: glucose, lactose, saccharose, etc. In addition or in substitution of the excipient, it is also possible to add to allergens one or more substances, which have a medical activity.

As far as capsules are concerned, they must preferably be of the hard type, and are also called operculates. Normally they consist of gelatine, moulded in such a way as to form two cylinders both closed at one end and perfectly fitting the one within the other, the delimiting a cavity in which the medicine or the excipient, containing the medicine, which in our case corresponds to the active principle of one or more allergens, remains endosed It is also possible to use capsules consisting of different materials, provided that they have similar characteristics and they are suitable for the use they are intended for. In fact, in practice, according to this invention, the capsules act not only as containers. Therefore it is not necessary that they consist of substances assimilable by the organism.

In the capsules of the present invention, the content of the allergen active principle can vary within a wide range: generally small quantities, ranging from some thousanths to some millionths grams per dose, are enough to obtain the wanted effect. The quantities of allergens, used in practice, vary in the range mentioned above, according to the type of allergen, object of the therapy, and what stage of therapy the patient has reached, as the hyposensitization therapy generally needs the administration of progressively increasing quantities of allergen. The excipient quantity to use is not critical and can vary substantially according to the allergen: for example between 1:1 and 50,000:1.

Tests performed by the Applicants have established that to obtain positive and constant results with hyposensitization, using the capsules subject of this invention, it is necessary, first of all, to use the active principle of the allergen and, moreover, that the dilution of the allergen in the excipient be homogeneous, is to say that the allergen must be uniformly diluted in the excipient mass. So, for example, if the dilution of the allergen in the excipient is carried out by stirring the dry state components, finely sub-divided, even if the stirring lasts a very long period (24 hours or more), it can happen that the mixture doesn't result to be perfectly homogeneous.

This can involve that the organic reactions of the patient to the inhalation of the same quantity of allergen-excipient mixture vary from time to time, and that, moreover, the patient shows anomalous and unwanted reactions, due to the inhalation of a greater quantity of allergen than necessary.

From this point of view even the process for the preparation of the dilution of the allergen in the excipient has a great importance.

The methods to prepare the allergen-excipient dilution, which allowed the Applicant to obtain optimum results in terms of activity and constant yield of the product, are the following ones.

METHOD (A)

An aqueous solution of the active principle of the allergen is diluted, under stirring at room temperature, in the excipient mass, for example lactose, in such a quantity as to cause either dissolution of the excipient or the formation of a wet mass, but rather the formation of a moist with the appearance and the consistency of powder.

Satisfactory results have been obtained diluting 125 ml. of the aqueous solution of the active principle in a mass of 1.000 grams of powdered lactose.

If the allergen is in the dry state, for example freeze-dried, it is diluted in a similar quantity of water.

The moist mass, so obtained, is accurately mixed and homogenised by means of repeated passages through a sieve with a rather large mesh size, for example a sieve with a mesh size of 500 miscrons.

The mass, so obtained, is dried at a temperature such as not to alter the product (30°–50° C.), for example by drying in a air-current oven. The powdered mass is finely refined by means of further passages through sieves with smaller and smaller meshes, for example by means of successive passages through stainless steel sieves with a mesh size of 180, 100 and 50 microns.

The product, so obtained, is distributed into rigid gelatine capsules, for example in quantity of 40 mg per capsule.

METHOD (B)

The excipient is diluted in 6 l. water. To the solution of the excipient is added the active principle of the allergen, either in solution or dehydrated, for example freeze-dried. The mixture is stirred for a long time (1–10 hours), till it reaches a perfect homogeneity. The solution so obtained is then dehydrated, preferably through freeze-drying.

The anhydrous mass so obtained is crushed in a mortar and then finely powdered either by repeated passages through sieves with progressively smaller meshes, as described for process (A) or by means of a micronizer, for example the one in which the break up of the material is obtained by a fluid jet mill.

Using a micronizer, it is possible to obtain a powder consisting of lactose and allergen, whose particles have the following dimensions: 90% are smaller than 10 microns and the remaining 10% smaller that 20 microns.

The finely powdered material so obtained is distributed into rigid gelatine capsules, for example in quantity of 40 mg. per capsule.

The administration to the patient of the active principle of the allergen, which is in the interior of the capsules, can be effected by inserting the capsules in anyone of the known bronchial inhalers or nasal sprays. The functioning of these inhalers and sprays varies from type to type, but it generally lies in the perforation of the capsule and in the emission of the powder through the holes, due to the suitable air flows.

The following examples are given for better illustrating the present invention without, however, limiting the scope thereof.

EXAMPLE 1

A culture of *Dermatophagoides pteronyssinus* supplied by ALLERGON AB, Engelholm-Sweden, having a purity of 95% by weight, detectable medium particles of 5%, detectable spores of 0%, total nitrogen content of 12,7% and Protein nitrogen content (conc. 1:10) of 196.000 PNU/ml, was suspended in a buffer solution of monobasic and dibasic sodium phosphate, having a concentration of 0.15M. and buffered at pH 7.2. The mixture was homogenized in the Sorwall homogenizer under stirring at 14,000 rpm for 3 min. The fine suspension was kept at +4° C., under stirring for 24 hours. The obtained suspension was centrifugated at 5,000 g for 30 min. and the clear supernatant was separated, dialyzed for 46 hours on the same buffer solution above reported and sterilized by filtration on Millipore membranes having 0.22 microns pores. The allergen solution was subjected to the following tests:

| | |
|---|---|
| Sterility test: | Negative |
| Titration of the proteic content: | 1.1 mg/ml |
| Titration of the allergenic content, according to the RAST based allergen assay method: (described in Develop Biol. standard Vol. 29 pp. 151-165 - 1975). | $C_{50} = 0.00023$ ml |

For the preparation of the capsules, the following ratios of allergen solution and powdered lactose were used:

| CAPSULES UNITS | ALLERGEN SOLUTION ml. | LACTOSE g. |
|---|---|---|
| 800 | 0.63 | 1 |
| 600 | 0.47 | 1 |
| 400 | 0.32 | 1 |
| 200 | 0.16 | 1 |
| 100 | 0.08 | 1 |
| 50 | 0.04 | 1 |

The allergen solution and the lactose were mixed in the above-reported ratios, to obtain a moist powder which was crushed in a crusher and passed through sieves having 500 microns meshes. The moist granulate was dried in an air current stove at 35° C. for a night and micronized by 5 passages through sieves being progressively smaller meshes of 180, 100 and 50 microns.

The finely powdered mixture so obtained, in which the allergen is incorporated in the lactose, is distributed into rigid gelatine capsules in quantity of 40 mg per capsule.

20 individuals with asthma caused by house dust mite (HDM) allergy, were tested by letting the individuals inhale the powder Dermatophagoides-lactose mixture contained in the above prepared capsules by means of SPINHALER. The SPINHALER is a commercially available bronchial inhaler manifactured by Fisons Corporation. Each individual inhaled one capsule at time by inhalation by oral route, according to the instructions of the SPINHALER manufacturer. The age and the sex of each individual and the obtained results are reported in the following Table I:

TABLE I

RESULTS OBTAINED WITH LOCAL HYPOSENSITIZATION

| Patient | Age | Sex | Cumulative dose | Maintenance dose | Anamnestic remarks | Clinical results |
|---|---|---|---|---|---|---|
| P.G. | 17 | F | 6,000 U.A. | 100 | Previous hyposensitization by subcutaneous route without clinical relief | Complete recovery |
| O.E. | 14 | M | 20,000 U.A. | 200 | Previous hyposensitization by subcutaneous route without clinical relief | Complete recovery |
| D.S.R. | 15 | F | 15,000 U.A. | 100 | | Marked improvement |
| P.Q. | 20 | F | 20,000 U.A. | 100 | Previous hyposensitization by subcutaneous route without clinical relief | Marked improvement |
| V.M. | 19 | M | 10,000 U.A. | 200 | | Complete recovery |
| L.G. | 17 | M | 20,000 U.A. | 200 | | Marked improvement |
| C.G. | 12 | M | 10,000 U.A. | 200 | | Poor improvement; therapy stopped |
| M.N. | 44 | F | 7,000 U.A. | 100 | Previous hyposensitization by subcutaneous route without clinical relief | Poor improvement; therapy stopped |
| F.F. | 21 | F | 7,000 U.A. | 200 | | Fairly good improvement |
| C.D. | 20 | F | 20,000 U.A. | 200 | Previous hyposensitization by subcutaneous route without clinical relief | Fairly good improvement |
| C.R. | 26 | F | 60,000 U.A. | 600 | Previous hyposensitization by subcutaneous route without clinical relief | Marked improvement |
| D.C.L. | 38 | F | 6,000 U.A. | 400 | | Recovered; the p. dropped out the therapy |
| S.M. | 13 | F | 20,000 U.A. | 100 | Previous hyposensitization by subcutaneous route without clinical relief | Marked improvement |
| S.A. | 14 | M | 30,000 U.A. | 200 | Previous hyposensitization by subcutaneous route without clinical relief | Marked improvement |
| V.M.N. | 24 | F | 25,000 U.A. | 100 | Previous hyposensitization by subcutaneous route without clinical relief | Complete recovery |
| D.A.F. | 56 | M | 60,000 U.A. | 600 | | Marked improvement |
| S.M. | 24 | M | 100,000 U.A. | 600 | | Complete recovery |
| C.C. | 22 | M | 50,000 U.A. | 400 | | Complete recovery |
| S.F. | 28 | M | 36,000 U.A. | 200 | Previous hyposensitization by subcutaneous route without clinical relief | Recovered; the p. dropped out the therapy |
| F.R. | 24 | M | 50,000 U.A. | 400 | Previous hyposensitization by subcutaneous route without | Very marked improvement |

TABLE I-continued
RESULTS OBTAINED WITH LOCAL HYPOSENSITIZATION

| Patient | Age | Sex | Cumulative dose | Maintenance dose | Anamnestic remarks | Clinical results |
|---------|-----|-----|-----------------|------------------|---------------------|------------------|
| | | | | | | clinical relief |

The treatment was carried out for a period of 6-12 months, with the following supply:
1st month: 1 inhalation/week The GRASS allergens were supplied by ALLERGON AB-Sweden and the composition of the mix is reported in the following table II:

TABLE II

| ALLERGEN | PURITY % b.w. | PLANT PARTS % b.w. | TOTAL NITROGEN CONTENT | PROTEIN NITROGEN CONTENT (PNU/ml) | ASH % | CONTENTS IN THE MIXTURE % b.w. |
|----------|---------------|--------------------|-----------------------|-----------------------------------|-------|-------------------------------|
| Timothy grass | 94 | 6 | 3.6 | 92,000 | 4.3 | 12.5 |
| Red Top grass | 87 | 13 | 3.9 | 57,050 | 5.6 | 12.5 |
| Orchard grass | 94 | 6 | 3.4 | 72,100 | 4.4 | 12.5 |
| Perennial rye grass | 92 | 8 | 4.4 | 85,470 | 5 | 12.5 |
| Velvet grass | 95 | 5 | 4.5 | 58,800 | 5.5 | 12.5 |
| Meadow Fescue grass | 90 | 10 | 4.6 | 109,000 | 4.7 | 12.5 |
| Bermuda grass | 90 | 10 | 3.4 | 52,000 | 7.6 | 12.5 |
| Blue grass Kentucky | 93 | 7 | 3.7% | 84,000 | 4.6 | 12.5 |

2nd month: 1 inhalation/week
3rd month: 1 inhalation/week
from the 4th month to the end of the treatment: 1 inhalation/10-15 days.

The results obtained and reported in the table I show that 80% of the tested patients, that is 16 patients, achieved either complete recovery or a very marked improvement and only 20%, that is only four patients, did not completely recover.

Some of the tested patients had been previously treated by the subcutaneous route with a solution of the same *Dermatophagoides pteronyssinus* prepared with material supplied by ALLERGON AB Sweden, according to the previously used therapy, but they had not reported any appreciable improvement.

The patients were carefully followed during the period of treatment with the capsules of the present invention and no broncho-constrictive action or irritation of bronchial mucous membrane was noted, even after 12 month treatment.

EXAMPLE 2

By operating according to the procedure of example 1, capsules containing Grass mix incorporated into lactose were prepared.

5 individuals, who suffered from asthma from grass allergins were tested by letting the individuals inhale the powder grass mix lactose mixture, contained in the capsules, by means of SPINHALER.

The age and the sex of each individual and the obtained results are reported in the following Table III:

TABLE III
RESULTS OBTAINED WITH CAPSULES CONTAINING GRASS ALLERGEN

| Patient | Age | Sex | Cumulative dose | Maintenance dose | Anamnestic remarks | Clinical results |
|---------|-----|-----|-----------------|------------------|---------------------|------------------|
| F.M. | 17 | F | 3,000 U.A. | 100 | Previous hyposensitization by subcutaneous route without clinical relief | Complete recovery |
| P.F. | 37 | M | 1,500 U.A. | 150 | Previous hyposensitization by subcutaneous route without clinical relief | Complete recovery |
| G.C. | 43 | M | 1,800 U.A. | 100 | Previous hyposensitization by subcutaneous route without clinical relief | Fairly good improvement |
| S.M. | 23 | F | 2,000 U.A. | 200 | Previous hyposensitization by subcutaneous route without clinical relief | Complete recovery |
| C.C. | 14 | F | 5,000 U.A. | 200 | Previous hyposensitization by subcutaneous route without clinical relief | Fairly good improvement |

The result show that 60% of the tested patients, that is 3 patients, achieved a complete recovery and the remaining patients achieved fairly good improvement.

The patients during the period of treatment did not suffer any broncho-constrictive action or irritation of the bronchial mucous membrane, even after a 12 month treatment.

In both the treatments with *Dermatophagoides pteronyssinus* and Grass mix, an increase in the bronchial tolerance was noted.

The obtained clinical results indisputably show that in the capsules, the allergen which is present in dry form, retains its activity over at least 12 months, and further, that the capsules are more effective in immunotherapy as compared with other preparations of allergens which have been used in immunotherapy. In this connection, the tested patients had been previously treated by the subcutaneous route with the same allergen preparation, according to the previously used therapy, but they had not reported any improvement.

The subcutaneous therapy had been stopped at least one year prior to inhalation of the allergen from the capsules according to the present invention.

Therefore, the improvement achieved must be attributed to the method used for the treatment rather than the previous subcutaneous therapy. The method of inhaling the allergen from the capsules is superior to other methods previously used and it is free of secondary reactions.

EXAMPLE 3

The same results described in Table III were obtained by the inhalation of a powder Ambrosia Elatior (short ragweed)-lactose mixture, prepared according to the process of Example 1, contained in capsules and inhalated by SPINHALER, to individuals suffering from asthma caused by Ambrosia Elation allergy.

The used Ambrosia Elatior was supplied by ALLERGON AB-Sweden and had a purity of 97% b.w.; a plant parts of 3% b.w.; a total nitrogen content of 4%; a protein nitrogen content of 82000 PNU/ml and an ash content of 3.7.

What we claim is:

1. A telescoping two piece hard gelatine capsule perforated to emit powder through the holes, to be administered through insertion in an inhaler, inhaler tube or nasal spray, containing 40 mgs. per capsule of a finely subdivided freeze dry, anhydrous powder mixture whose particles are 90% smaller than 10 microns and the remainder 10% smaller than 20 microns of the active constituent of an allergen, which is a member selected from the group consisting of *Dermatophagoides pteronyssinus, Dermatophagoides farinae, Ambrosia elatior, Agrostis maritima, Agrostis stolonifera, Poa pratensis, Dactylis glomerata, Holcus lamatus, Phleum pratense, Phalaris Canariensis, Lolium perenne, Lolium multiflorum, Festuca pratensis, Festuca ovina, Cynodon dactylon* and *Agarostis alba.,* said active constituent being uniformly dispersed into at least one lactose glucose or saccharose excipient having no brochoconstrictive or irritating action on the nasal mucous membrane in a ratio of excipient to allergen between 1:1 and 50,000:1.

2. A method of administration of an allergen to an individual who suffers from an allergy, which consists of administering to said individual a powder by emission through the holes of a perforated telescoping two piece hard gelatine capsule inserted in an inhaler or inhaler tube or nasal spray, said capsule containing 40 mgs. of a freeze dry, anhydrous powder which consists of a mixture whose particles are 90% smaller than 10 microns and the remainder 10% smaller than 20 microns of the active constituent of an allergen which is a member selected from the group consisting of *Dermatophagoides pteronyssinus, Dermatophagoides farinae, Ambrosia elatior, Agrostis maritima, Agrostis stolonifera, Poa pratensis, Dactylis glomerata, Holcus lamatus, Phleum pratense, Phalaris canariensis, Lolium perenne, Lolium multiflorum, Festuca pratensis, Festuca ovina, Cynodon dactylon* and *Agrostis alba.,* said active constituent being uniformly dispensed in at least one lactose, glucose or saccharose excipient having no bronchoconstriction and irritation actions on the nasal mucous membrane, in a ratio of excipient to allergen between 1:1 and 50,000:1, said dry powder having a particle size lower than 50 microns.

3. The method according to claim 2 wherein the allergen is *Dermotophagoides pteronyssinus.*

4. The method according to claim 2, wherein the allergen is *Dermatophagoides farinae.*

5. The method according to claim 2, wherein the allergen is a Grass allergen or a mixture of Grass allergens.

6. The method according to claim 2, wherein the allergen is Ambrosia Elatior.

7. A capsule according to claim 1, wherein the quantity of the active constituent of said allergen in each capsule ranges from 1.8 millionth to 28 millionths of a gram.

* * * * *